Figure 1:
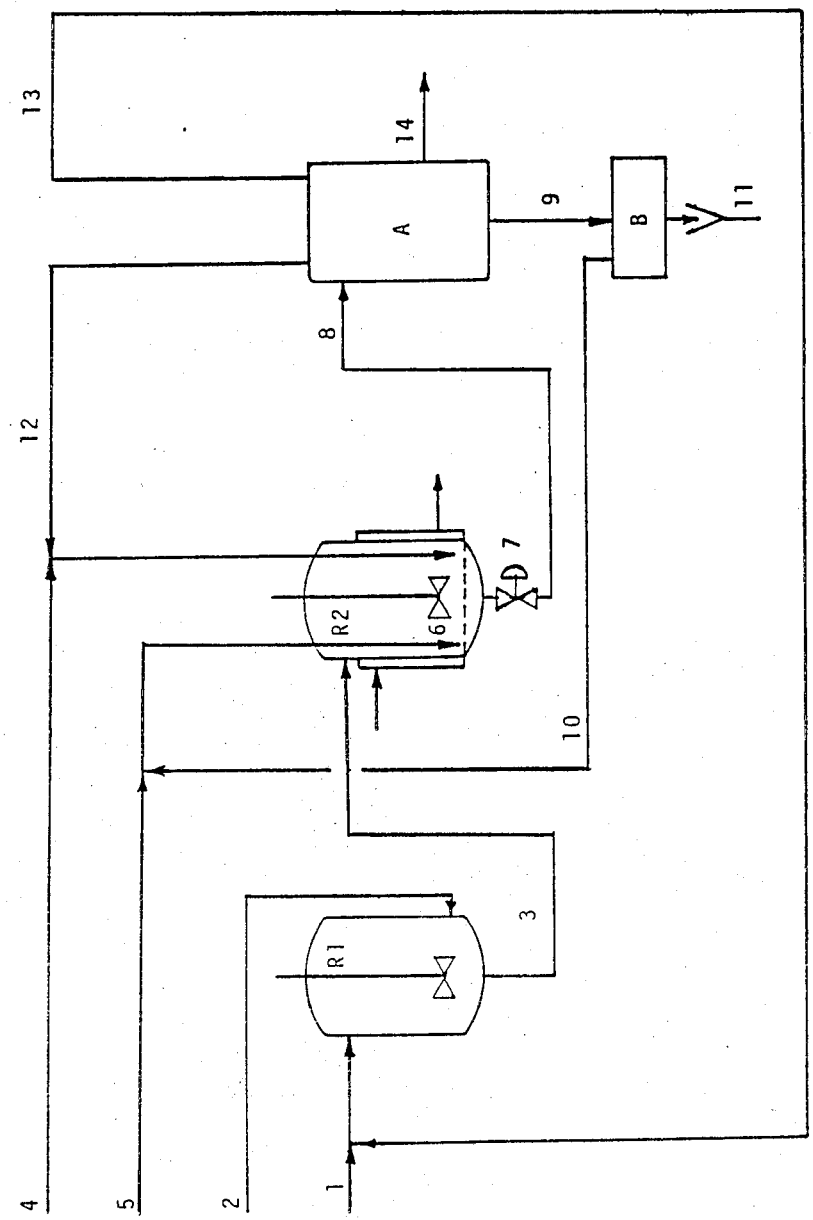

United States Patent [19]

Roffia et al.

[11] Patent Number: 4,894,478

[45] Date of Patent: Jan. 16, 1990

[54] PROCESS OF PRODUCING KETOXIMES

[75] Inventors: Paolo Roffia, Saronno; Giuseppe Paparatto, Cinisello Balsamo; Alberto Cesana, Carate Brianz; Giorgio Tauszik, Milan, all of Italy

[73] Assignee: Montedipe S.p.A., Milan, Italy

[21] Appl. No.: 223,403

[22] Filed: Jul. 25, 1988

[30] Foreign Application Priority Data

Jul. 29, 1987 [IT] Italy .............................. 21493 A/87

[51] Int. Cl.$^4$ ............................................ C07C 131/04
[52] U.S. Cl. ..................................... 564/267; 564/253; 564/265; 564/266; 564/268; 568/357; 568/402
[58] Field of Search ............... 564/259, 267, 253, 265, 564/266, 268; 568/357, 402

[56] References Cited

U.S. PATENT DOCUMENTS

| 4,002,685 | 1/1977 | Charles et al. | 568/402 |
| 4,250,121 | 2/1981 | Mimoun | 568/402 |
| 4,794,198 | 12/1988 | Roffia et al. | 564/253 |

FOREIGN PATENT DOCUMENTS

| 208311 | 1/1987 | European Pat. Off. | 564/253 |
| 1113687 | 5/1968 | United Kingdom | 568/402 |
| 1318525 | 5/1973 | United Kingdom | 568/402 |
| 1421449 | 1/1976 | United Kingdom | 568/402 |

OTHER PUBLICATIONS

Neginskaya et al., Z. Prik. Khimii, vol. 58, pp. 2512-2516, (1985).

Primary Examiner—James H. Reamer
Attorney, Agent, or Firm—Stevens, Davis, Miller & Mosher

[57] ABSTRACT

The invention relates to a process of producing ketoximes, characterized in that a secondary alcohol, corresponding to the desired ketoxime, is partially oxidated in the liquid phase with $O_2$, an oxidated mixture being thereby formed, which contains an excess of unreacted alcohol, the ketone corresponding to said alcohol, and $H_2O_2$, and that said oxidated mixture is directly reacted with $NH_3$ in the liquid phase (without isolating the alcohol, the ketone and $H_2O_2$) in the presence of an ammoximation catalyst.

14 Claims, 2 Drawing Sheets

PROCESS OF PRODUCING KETOXIMES

BACKGROUND OF THE INVENTION

From German patent 12 45 371, the obtainment is known of cyclohexanone-oxime by means of the catalytic reaction in the liquid phase of cyclohexanone with $NH_3$ and $H_2O_2$ (ammoximation reaction), at 5°–40° C., in the presence of a catalyst constituted by phosphotungstic acid, or by similar compounds. This type of catalyst, however, is difficult to handle, above all during the step of separation of the product from the catalyst, and European patent publication 208 311 teaches an efficacious alternative route, constituted by the catalysis with a titanium-silicalite, of the type disclosed, e.g., in U.S. Pat. Nos. 4,410,501 and 4,480,135 and in European patents 132 550, 190 609 and 200 260. A particular type of post-treatment with $H_2O_2$ of the titanium-silicalites (or of zirconium-silicalites) can endow them with exceptional and quite surprising catalytic properties in the reaction of ammoximation of various carbonylic compounds (see European patent application 87/108,577). A disadvantage of the heretofore used technique is however the need of providing, upstream an ammoximation facility, at least two further synthesis facilities, and namely:

a facility for cyclohexanone synthesis, generally by cyclohexaol dehydrogenation in the gas phase, also comprising an efficacious distillation section, in order to separate cyclohexanone from unreacted cyclohexanol;

a facility for the synthesis of hydrogen peroxide, which usually requires the presence of a (more or less hydrogenated) antraquinonic vehicle, a high hydrogen consumption and a complex series of operations.

The Applicant has now surprisingly found that the need of a facility for the ketone production from its corresponding alcohol, as well as of a separate facility for the $H_2O_2$ production from $H_2$ and $O_2$ can be overcome at all, the complexity of the operations being drastically reduced.

DISCLOSURE OF THE INVENTION

In its broadest aspect, the invention consists of a process (for ketoxime production) characterized in that:

(a) a secondary alcohol, corresponding to the desired ketoxime, is partially oxidated in the liquid phase (with oxygen, or with another gas, containing oxygen), an oxidated mixture being thereby formed, which contains an excess of unreacted alcohol, the ketone corresponding to said alcohol and hydrogen peroxide;

(b) said oxidated mixture is directly reacted with ammonia in the liquid phase, in the presence of an ammoximation catalyst.

Information on the catalyst and on the operating conditions for the ammoximation can be found in the patents hereinabove. Information as to the partial oxidation in the liquid phase of cyclohexanol (also called: "self-oxidation") and on the consequent oxidated mixture, also containing, besides alcohol, ketone and $H_2O_2$, a few organic hydroperoxides and peroxides, as well as carboxylic acids (very undesired) can also be found in the relevant literature; see, e.g. U.S. Pat. Nos. 2,869,989; 2,871,104; and 3,592,776; U.K. patent 1,318,525; German patent 1,002,295; Canadian patent 1,003,189 and a paper by R. V. Neginskaya et al., published on Zhurnal Prikladnoi Khimii, November 1985 (volume 58, No 11, pages 2512-2516). The contents of these documents are incorporated herein by reference in their entirety.

These documents teach that the partial oxidation of a secondary alcohol with $O_2$ (in the liquid phase, and, possibly, in the presence of a free-radical initiator) not only causes the formation of the corresponding ketone and of $H_2O_2$, but also of substances having hydroperoxidic and/or peroxidic character, e.g., according to the schematic equation:

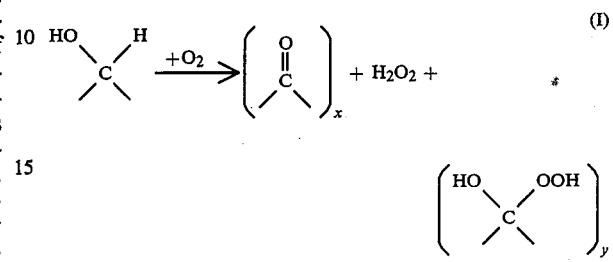

wherein $(x+y)=1$. However, the literature in this field (see, e.g., U.K. patent 1,113,687) is suggesting the most efficacious methods for isolating the unreacted alcohol, the ketone, $H_2O_2$ and, above all, the carboxylic acids, in order to prevent $H_2O_2$ decomposition and a negative impact on the reactions downstream this step.

The Applicant has now surprisingly found that the titanium-silicalites cause the impurities above not to hinder the specific realization of the ammoximation, and hence enable said oxidated mixture to be "directly" used, without the alcohol, ketone, $H_2O_2$ being isolated in the pure state. The alcohol conversion is generally from 5 to 50% and the amount of said carboxylic acids is generally from 0.001 to 15%, and preferably of from 0.001 to 5%, by weight, on the ketone. The alcohol conversion can be increased to even higher levels (than said 50% level) if a suitable diluent solvent, e.g., tert-butyl alcohol, is present.

The consequence of this discovery, unexpected from all viewpoints, are of a tremendous importance, both in terms of reduction in plant complexity, and in terms of raw material saving. The advantage of the invention consists in fact precisely in that when as the starting compound is a secondary alcohol, precursor of the desired ketone, the use of separately synthetized $H_2O_2$ is no longer necessary, the basic oxidant raw material being constituted by such a much easier available oxidant as oxygen.

The secondary alcohols suitable for the self-oxidation have, e.g., the formula:

wherein $R_1$ and $R_2$ are alkyl, cycloalkyl or aryl groups, or are a part of a cycloaliphatic ring, optionally containing heteroatoms, said alcohols being also optionally substituted with oxidation-stable substituting groups, such as the carboxylic groups (optionally as esters), alkoxy groups, and so forth. 2-Butanol, 3-pentanol, cyclopentanol, cyclohexanol and methylphenyl-carbinol may be cited for exemplifying purposes. The "self-oxidation" can be carried out on the alcohols in pure form, or on a mixture obtained by dilution with an inert solvent, e.g., water, tert.-butyl alcohol, benzene, and so forth, and is advantageously carried out inside a stirred reactor, whose walls are constituted by materials compatible with the presence of hydrogen peroxide. The self-oxidation reaction is in fact carried out under stirring, in order to cause a good contact to occur between the liquid phase and the gas phase (which contains oxygen). The oxidation temperature is generally from 50° to 150° C., preferably from 80° to 120° C., and the pressure shall be such that the reactants and the oxidation products remain in the liquid phase; the pressure values can be generally from 1 to 100 bars, and preferably of from 1 to 50 bars. The secondary alcohol self-oxidation process can be carried out continuously or batchwise; in this latter case, it is suitable to operate in the presence of a suitable reaction initiator, selected from the compounds commonly used for oxidations of a radicalic type. For merely exemplifying purposes, azo-bis-isobutyronitrile, or the same hydrogen peroxide may be cited; the relevant literature (see, e.g., U.S. Pat. No. 2,871,104; German patent 10 02 295 and U.K. patent 1,421,449) also teaches to operate in the presence of agents capable of stabilizing $H_2O_2$ (e.g., potassium metaphosphate or pyrophosphate, ammonium nitrate and their mixtures; see also U.S. Pat. No. 4,320,102). Sometimes, the self-oxidation can be advantageously carried out in a plurality of steps in series, with the reactants feed being optionally subdivided; in this case, a gradual temperature decrease form step to step is recommended.

The ammoximation reaction can be carried out, either batchwise or as a continuous process, in a reactor, to which the catalyst is charged, said catalyst being preferably constituted by a titanium-silicalite, i.e., a crystalline and porous synthetic material, having a zeolitic structure, containing Si, Ti and oxygen in combined form and having, differently from simple silicalite, a characteristic band in its I.R. spectrum, situated at about 950 $cm^{-1}$ (see, in this regard, U.S. Pat. No. 4,410,510). To the reactor, from two different feed lines, the mixture obtained from the self-oxidation of the secondary alcohol and ammonia (either as a gas, or dissolved in aqueous solution) arrive simultaneously. The ammoximation reaction occurs only inside the reactor, where the catalyst is present, and where the temperature is controlled at an optimum level (25°–150° C., preferably 40°–120° C., and still better from 60° to 120° C.); tests run at 15° C. gave not very satisfactory results. The reaction can be carried out under atmospheric or slightly superatmospheric pressure, in order to keep dissolved in the reaction medium an $NH_3$ amount at least equal to the amount required by the synthesis. The catalyst can be arranged on a fixed bed, or it can be finely dispersed in the reaction medium (suspended bed), provided reactors having surfaces compatible with the presence of hydrogen peroxide are used. If the process is carried out batchwise, from 0.5 to 100 parts by weight (preferably from 1 to 100 parts) of pure catalyst, excluding the binder, per 100 parts by weight of ketone should be used; when the process is run in a continuous way, a space velocity from 0.1 to 100 kg/hour of ketone (as defined above) per kg of pure catalyst (excluding the binder) is suggested. The active oxygen:ketone molar ratio should be generally from 0.8 to 1, and preferably from 0.9 to 1, wherein by the term "active oxygen" the (molar) sum of $H_2O_2$ and of the above-mentioned peroxidic and hydroperoxidic organic compounds is meant. The $NH_3$:$H_2O_2$ molar ratio should be equal to, or higher than, 1 (preferably, 1.5), otherways parallel disturbing reactions occur. The reaction medium can be constituted by water, or by a water-miscible organic solvent; really outstanding results were obtained when as the solvent tert.-butyl alcohol, or the same cyclohexanol, were used. Very good results were obtained when in the ammoximation a titanium-silicalite was used, which previously underwent a particular type of $H_2O_2$-based post-treatment, of such a type as disclosed in European patent application 87/108,577 and in Italian patent application 21,266 A/87, the contents of which are incorporated herein by reference in their entirety. The oximes which can be obtained by means of this process are, e.g., cyclohexanone-oxime (from cyclohexanol), methyl-ethyl-ketone-oxime (from 2-butanol), cyclo-dodecanone-oxime (from cyclo-dodecanol) and acetophenone-oxime (from methyl-phenyl-carbinol).

The oxime can be recovered from the ammoximation reaction product by several ways, e.g., by extraction with suitable solvents (e.g., benzene, toluene, and the same secondary alcohol as used for the self-oxidation), with a hydrophobic organic phase and an aqueous phase being thereby obtained. The oxime and the unreacted secondary alcohol are contained in the organic layer: the secondary alcohol can be recovered and recycled to oxidation, and $NH_3$ can be recovered from the aqueous phase and recycled to the ammoximation. As an alternative, the extraction may take place simultaneously to the oxime formation, by operating in a biphasic system; this system can be advantageously realized by using a couple of solvents having different characteristics, e.g., blends of tert.-butanol (and/or cyclohexanol, i.e., hydrophilic compounds) with toluene (a hydrophobic compound).

The invention is now also illustrated by referring to figures, which however in no way limit the scope of the invention.

Referring to FIG. 1, a secondary alcohol (1), optionally diluted with water or another solvent, and an oxygen stream (2) enter the reactor $R_1$, equipped with a rotary-blade stirrer. The consequent oxidated mixture (3) contains the unreacted alcohol, the corresponding ketone and $H_2O_2$, as well as the optional solvent charged together with the alcohol. Said oxidated mixture is transferred to the ammoximation reactor $R_2$ (which contains the catalyst), equipped with a temperature-control jacket and with a rotary-blade stirrer, fed, through a dipleg, with a stream of tert.-butanol (4) whereinto the catalyst is suspended. $NH_3$ is fed, in the gas form or as an aqueous solution, through the line (5), by means of a dipleg. A porous wall (6) keeps the catalyst suspended, and a valve (7) controls the level of the liquid inside the reactor and the flowrate of the raw ammoximation effluent (8), which flows to a separation area (A), wherein an extractor (not shown in figure) enables the aqueous phase (9), containing possible by products, which are removed from the cycle, to be discharged. A second separation area (B) makes it possible the ammonia excess (10) to be recovered; the recovered ammonia is recycled to the ammoximation reactor, and waste water (11) is removed. The organic phase is subdivided, according to usual techniques, into a tert.-butanol stream (12), which is recycled to the ammoximation reactor, a stream of unreacted secondary alcohol (13), which is recycled to the reactor $R_1$, where the oxidated mixture (3) is formed, and a stream of oxime (14), which is the desired product.

Figure 2:
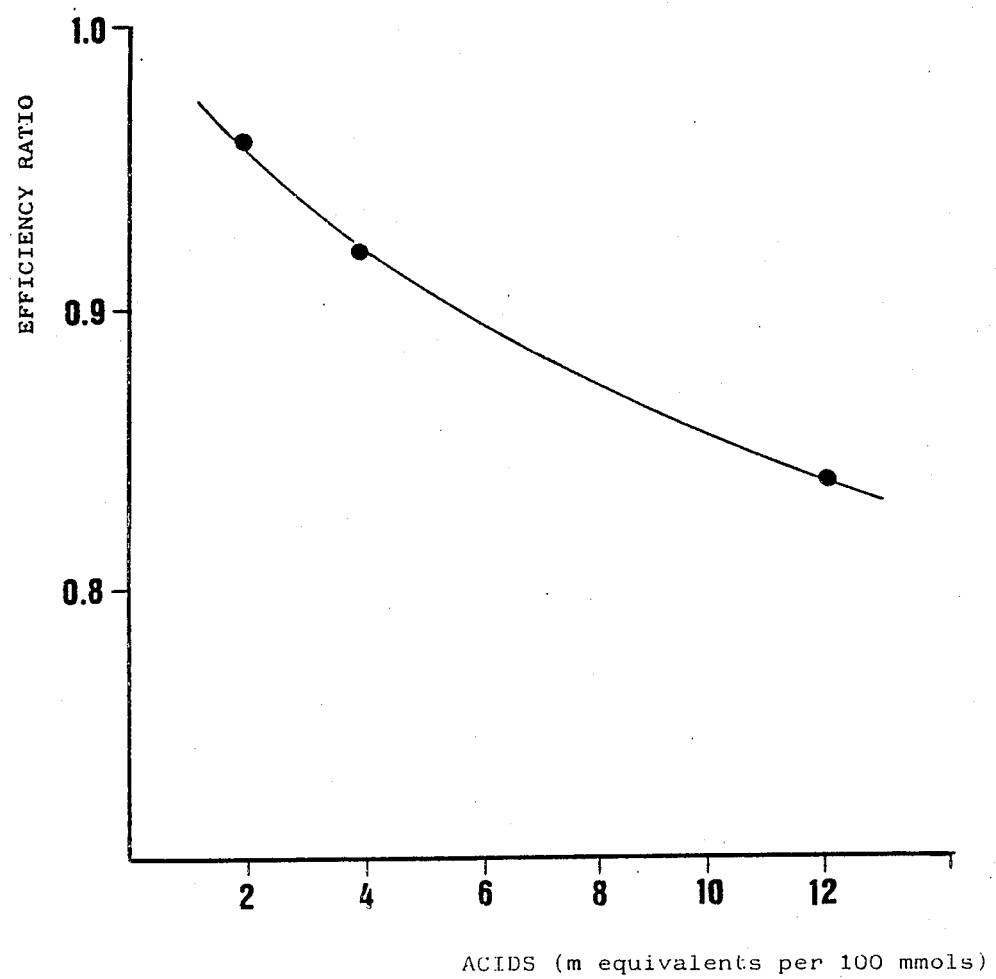

FIG. 2 shows an experimental chart, which shows how the efficiency ratio of the self-oxidation reactions (defined in the following) is strongly reduced when the concentration of the carboxylic acids is too high.

The following examples illustrate the present invention, without however limiting in any way the scope thereof.

EXAMPLE 1

(Preparation of the Ammoximation Catalyst)

544 g of tetraethyl orthosilicate were charged to a pyrex-glass, flame-resistant flask equipped with stirrer, and maintained under an inert atmosphere of nitrogen. Then, 24 g of tetraisopropyl titanate was added, and then 1,200 g of an aqueous solution of tetrapropylammonium hydroxide at 20% by weight was slowly added dropwise. The mixture was kept stirred for 1 hour at room temperature, and was then allowed to rest, still at room temperature, for a further hour. The temperature was slowly increased to 78° C., in order to eliminate ethyl alcohol, and was subsequently increased to 98° C., in order to remove isopropyl alcohol. The operation of removal of the alcohols developed during the reaction was carried out under stirring in 5 hours. After cooling, the volume of the liquid was increased to 2 liters by adding deionized water, and the (homogeneous and opalescent) solution was transferred to an autoclave equipped with a stirrer, inside which the hydrothermal synthesis was realized at 175° C. within a 10-day time, under the autogenous pressure. At the end, after cooling, the synthesis mixture was filtered and the solid product was washed for a long time, to neutral pH, and was dried at 120° C. for 15 hours. The dried product was finally calcined at 420° C. for 10 hours. The calcined product was placed in a glass, and was mixed with an aqueous solution, prepared by pouring 100 cm³ of hydrogen peroxide (at 30% by weight) with 1,000 cm³ of diluted sulphuric acid (at 5% by weight); the mixing operation ("activating washing") was continued for 2 hours at 70° C., and the liquid was then decanted off. The operation was further repeated twice, with fresh solutions, and after the last washing a filtration was carried out, which was followed by a long-time washing with deionized water (to neutral pH), and the product was dried at 120° C. for 15 hours; the product was finally calcined at 550° C. for 2 hours.

EXAMPLE 2

40 g of cyclohexanol and 0.4 g of free-radical initiator (azo-bis-isobutyronitrile), to which 100 ppm of potassium pyrophosphate and 20 ppm of ammonium nitrate were added, were charged to a temperature-controlled glass autoclave, of 200 cm³ of capacity, and equipped with a stirrer. After pressurization with oxygen, the temperature of the liquid was increased to 90° C. and sufficient amounts of oxygen were then fed (every 10 minutes) in order to maintain a constant pressure level (of approximately 2 bar). After 135 minutes of oxidation, always at 90° C., the reaction mixture was quickly cooled down to room temperature, the residual gases were vented off, and the same mixture was discharged. The gas-chromatographic analysis made it possible to ascertain that the conversion to cyclohexanol was 4.9%, with a 96% selectivity to cyclohexanone, the selectivity to active oxygen ($H_2O_2$+hydroperoxidic and peroxidic organic compounds) being of 96%, and that the acidity, as carboxyl acids, was 1.5 milliequivalents per 100 millimol of ketone. The efficiency ratio (R):

$$R = \frac{H_2O_2}{(H_2O_2 + \text{peroxidic and hydroperoxidic organic forms})}$$

was 0.965 (by mols); these data are reported in Table 1.

The thus obtained oxidated mixture was used for the ammoximation reaction. For that purpose a glass reactor, equipped with stirrer and cooling jacket, was pressurized with an inert gas (nitrogen). Then 1 g of fine titanium-silicalite powder, prepared according to example 1, 25 g of tert.-butyl alcohol, 10.5 g of $H_2O$ and 2 g of $NH_3$ were charged. The stirring was started, and the temperature was increased to 80° C., by circulating a diathermal fluid through the reactor jacket; then the feed of the oxidated mixture to the reactor, by means of a metering pump, was started. The addition was continued for 5 hours, and an overall amount of 25.9 g of solution was fed; during the addition, a decrease in pressure took place. The reaction suspension was cooled to room temperature, to it ethyl ether was added, and the suspension was stirred for some minutes; the aqueous phase and the ethereal phase were then separated from the catalyst by filtration, and the liquid phases were finally separated from each other (by a dripping funnel). The analysis supplied the results are listed in Table 2.

EXAMPLE 3

The self-oxidation of Example 2 was repeated, cyclohexanol being replaced by 40 g of a solution containing cyclohexanol and water (according to a ratio of 95/5 by weight) the reaction temperature being increased to 100° C.; after 3 hours, the cyclohexanol conversion was 8.8% and the corresponding selectivity to cyclohexanone was 98%, the selectivity to active oxygen ($H_2O_2$+hydroperoxidic and peroxidic organic compounds) being 95%. The other results of cyclohexanol self-oxidation are shown in Table 1.

The thus obtained oxidated mixture was used for the ammoximation reaction, according to the same modalities as shown in Example 2; the results are reported in Table 2.

EXAMPLE 4

A mixture containing 300 g of cyclohexanol, 1.5 g of free-radical initiator (azo bis-isobutyronitrile) and 15 g of $H_2O$, to which 100 ppm of potassium pyrophosphate and 20 ppm of ammonium nitrate were added, was charged to a temperature-controlled glass autoclave of 500 cm³ equipped with a gaseous-effect stirrer. After pressurizing with oxygen to 5 bar, the temperature was increased to 110° C. The oxygen pressure was then increased to 8 bar, and was maintained at this level, with replenishments every 5 minutes. After a reaction time of 90 minutes, always at 110° C., the mixture was rapidly cooled down to room temperature, and was analysed. The conversion of cyclohexanol was 11.2% and the corresponding selectivity to cyclohexanone was 98.5%. The selectivity to active oxygen ($H_2O_2$+organic hydroperoxidic or peroxidic compounds) was 96%; the other results of the self-oxidation are reported in Table 1. The thus obtained oxidated mixture was used for the ammoximation reaction according to the same conditions as shown in Example 2; the results are reported in Table 2.

EXAMPLE 5

The self-oxidation of Example 2 was repeated, the following reactants being used:
25 g of cyclohexanol;
25 g of a solution of water in tert.butyl-alcohol, wherein the water:alcohol ratio was of 1:10 by weight;
0.25 g of initiator (azo-bis-isobutyronitrile),
the temperature being maintained at 100° C. After 4 hours, 13% of cyclohexanol had been converted, and the corresponding selectivity to cyclohexanone was higher than 97%, the selectivity to hydrogen peroxide (and other peroxidic forms) being approximately 95%; the other results of the self-oxidation are reported in Table 1. The thus obtained oxidated mixture was used in the ammoximation reaction according to such conditions as shown in Example 2; the results are reported in Table 2.

EXAMPLE 6

The self-oxidation of Example 2 was repeated, the temperature being increased to 110° C.; the results are reported in Table 1. The thus obtained oxidated mixture was used in the ammoximation reaction, according to the same conditions as shown in Example 2; the results are reported in Table 2.

TABLE 1

| Example | * | 2 | 3 | 4 | 5 | 6 |
|---|---|---|---|---|---|---|
| Cyclohexanol | (g) | 40 | 38 | 300 | 25 | 40 |
| Initiator | (g) | 0.4(*) | 0.4(*) | 1.5(*) | 0.25(*) | 0.4(*) |
| Temperature | (°C.) | 90 | 100 | 110 | 100 | 110 |
| Pressure | (bar) | 2 | 2 | 8 | 2 | 2 |
| Reaction Time | (minutes) | 135 | 180 | 9 | 240 | 135 |
| $H_2O$ | (g) | — | 2 | 15 | 25 × (1:11) | — |
| tert.-Butanol | (g) | — | — | — | 25 × (10:11) | — |
| Cyclohexanol Conversion | (%) | 5.1 | 8.8 | 11.2 | 13 | 9.5 |
| Carboxylic Acids | (meq per 100 ketone mol) | 1.5 | 2.5 | 2.0 | 4 | 12 |
| Selectivity to Ketone | | 96% | 98% | 98.5% | 97% | 92% |
| Selectivity to Active Oxygen | | 96% | 95% | 96% | 95% | 88% |
| Efficiency Ratio | | 0.965 | 0.950 | 0.960 | 0.920 | 0.820 |

(*) Azo-bis-isobutyronitrile

TABLE 2

| Example | | 2 | 3 | 4 | 5 | 6 |
|---|---|---|---|---|---|---|
| Ketone Conversion | (%) | 85.7 | 91.1 | 89.2 | 89 | 75.5 |
| Selectivity to Oxime | (%) | 94.7 | 84.7 | 95 | 93 | 95 |
| Active Oxygen Conversion | (%) | 97.4 | 98.2 | 98 | 98 | 97 |
| Active Oxygen Decomposition | (%) | 16.2 | 18.6 | 11 | 13 | 22 |
| Oxime Yield, Relatively to Active Oxygen | (%) | 81.2 | 79.6 | 87 | 85 | 75 |

What we claim is:

1. A process for the manufacture of cyclohexanone-oxime characterized in that:
   (a) cyclohexanol is subjected to a partial low-temperature oxidation in the liquid phase, by means of oxygen or an oxygen-containing gas, an oxidized mixture being thereby formed which contains an excess of unreacted cyclohexanol, the ketone corresponding to said cyclohexanol, hydrogen peroxide, and organic compounds having a hydroperoxidic and/or peroxidic structure; and
   (b) directly reacting said oxidized mixture with ammonia in the liquid phase, in the presence of an ammoximation catalyst consisting essentially of a titanium-silicalite, the oxidation temperature being from 50° to 150° C.

2. Process according to claim 1, wherein the degree of conversion of the cyclohexanol is within the range of from 5 to 50%.

3. Process according to claim 1 or 2, wherein said oxidized mixture contains also organic compounds having a hydroperoxodic and/or peroxidic structure.

4. Process according to claim 1 or 2, wherein said oxidized mixture contains also carboxylic acids and wherein the amount of said acids is from 0.001 to 15% by weight, based on said ketone.

5. Process according to claim 1 or 2, wherein said oxidized mixture contains also carboxylic acids and wherein the amount of said acids is from 0.001 to 5% by weight, based on said ketone.

6. Process according to claim 1 or 2, wherein the partial oxidation of the cyclohexanol is carried out in the presence of an inert solvent at a temperature from 50° to 150° C., and under a pressure from 1 to 100 bar.

7. A process as in claim 2, wherein the inert solvent is selected from the class consisting of water, tert.butyl alcohol, benzene and their mixtures, and under a pressure from 1 to 50 bar.

8. Process according to claim 1 or 2, wherein the partial oxidation of the cyclohexanol is carried out in the presence of a free-radical initiator.

9. A process as in claim 8, wherein the free-radical initiator is selected from the class consisting of $H_2O_2$, azo-bis-isobutyronitrile and their mixtures.

10. Process according to claim 1 or 2, wherein the partial oxidation of the cyclohexanol is carried out in the presence of a stabilizing agent in order to prevent hydrogen peroxide decomposition.

11. A process as in claim 10, wherein the stabilizing agent is selected from the class consisting of potassium metaphosphate, potassium pyrophosphate, ammonium nitrate and their mixtures.

12. Process according to claim 1 or 2, wherein the partial oxidation of the cyclohexanol is carried out according in a plurality of steps in series, with a decreasing profile of the temperatures in each individual step.

13. Process according to claim 1 or 2, wherein said titanium-silicalite, optionally diluted with inert material, is in the form of extruded granules, optionally polylobated and optionally showing helical grooves.

14. Process according to claim 1 or 2, wherein said titanium-silicalite, optionally diluted with inert material, is treated, before being used, with an activating washing based on hydrogen peroxide, after which the treated catalyst is dried and calcined.

* * * * *